US008426457B2

(12) United States Patent
Miller et al.

(10) Patent No.: US 8,426,457 B2
(45) Date of Patent: Apr. 23, 2013

(54) METHODS OF IMPROVING SKIN QUALITY

(75) Inventors: Richard L. Miller, Maplewood, MN (US); James H. Lee, St. Paul, MN (US); Mary L. Owens, Cottage Grove, MN (US)

(73) Assignee: Medicis Pharmaceutical Corporation, Scottsdale, AZ (US)

( * ) Notice: Subject to any disclaimer, the term of this patent is extended or adjusted under 35 U.S.C. 154(b) by 790 days.

(21) Appl. No.: 10/799,999

(22) Filed: Mar. 12, 2004

(65) Prior Publication Data

US 2004/0180919 A1    Sep. 16, 2004

Related U.S. Application Data

(60) Provisional application No. 60/454,245, filed on Mar. 13, 2003.

(51) Int. Cl.
*A01N 43/52* (2006.01)
*A01N 43/42* (2006.01)
*A61K 31/415* (2006.01)
*A61K 31/44* (2006.01)

(52) U.S. Cl.
USPC .......................................... 514/393; 514/291

(58) Field of Classification Search ............... 514/219, 514/844, 858–865, 393, 291
See application file for complete search history.

(56) References Cited

U.S. PATENT DOCUMENTS

| | | | |
|---|---|---|---|
| 4,689,338 A | 8/1987 | Gerster | |
| 4,698,348 A | 10/1987 | Gerster | |
| 4,929,624 A | 5/1990 | Gerster et al. | |
| 4,988,815 A | 1/1991 | Andre et al. | |
| 5,037,986 A | 8/1991 | Gerster | |
| 5,175,296 A | 12/1992 | Gerster | |
| 5,238,944 A | 8/1993 | Wick et al. | |
| 5,266,575 A | 11/1993 | Gerster et al. | |
| 5,268,376 A | 12/1993 | Gester | |
| 5,346,905 A | 9/1994 | Gerster | |
| 5,352,784 A | 10/1994 | Nikolaides et al. | |
| 5,367,076 A | 11/1994 | Gerster | |
| 5,376,501 A | 12/1994 | Mariën et al. | |
| 5,389,640 A | 2/1995 | Gerster et al. | |
| 5,395,937 A | 3/1995 | Nikolaides et al. | |
| 5,446,153 A | 8/1995 | Lindstrom et al. | |
| 5,482,936 A | 1/1996 | Lindstrom | |
| 5,494,916 A | 2/1996 | Lindstrom et al. | |
| 5,525,612 A | 6/1996 | Gerster | |
| 5,576,018 A * | 11/1996 | Kim et al. ..................... 424/450 |
| 5,605,899 A | 2/1997 | Gerster et al. | |
| 5,693,811 A | 12/1997 | Lindstrom | |
| 5,736,553 A | 4/1998 | Wick et al. | |
| 5,741,908 A | 4/1998 | Gerster et al. | |
| 5,756,747 A | 5/1998 | Gerster | |
| 5,939,090 A | 8/1999 | Beaurline et al. | |
| 6,028,076 A | 2/2000 | Hirota et al. | |
| 6,039,969 A | 3/2000 | Tomai et al. | |
| 6,069,149 A | 5/2000 | Nanba et al. | |
| 6,083,505 A | 7/2000 | Miller et al. | |
| 6,110,929 A | 8/2000 | Gerster et al. | |
| 6,113,918 A | 9/2000 | Johnson et al. | |
| 6,147,086 A | 11/2000 | Brenman | |
| 6,194,388 B1 | 2/2001 | Krieg et al. | |
| 6,194,425 B1 | 2/2001 | Gerster et al. | |
| 6,200,592 B1 | 3/2001 | Tomai et al. | |
| 6,207,646 B1 | 3/2001 | Krieg et al. | |
| 6,239,116 B1 | 5/2001 | Krieg et al. | |
| 6,245,776 B1 | 6/2001 | Skwierczynski et al. | |
| 6,303,347 B1 | 10/2001 | Johnson et al. | |
| 6,323,200 B1 | 11/2001 | Gerster et al. | |
| 6,329,381 B1 | 12/2001 | Kurimoto et al. | |
| 6,331,539 B1 | 12/2001 | Crooks et al. | |
| 6,335,023 B1 * | 1/2002 | Yu et al. ..................... 424/401 |
| 6,339,068 B1 | 1/2002 | Krieg et al. | |
| 6,365,166 B2 | 4/2002 | Beaurline et al. | |
| 6,376,501 B1 | 4/2002 | Isobe et al. | |
| 6,376,669 B1 | 4/2002 | Rice et al. | |
| 6,387,938 B1 | 5/2002 | Mizuguchi et al. | |
| 6,406,705 B1 | 6/2002 | Davis et al. | |
| 6,426,334 B1 | 7/2002 | Agrawal et al. | |
| 6,440,992 B1 | 8/2002 | Gerster et al. | |
| 6,451,810 B1 | 9/2002 | Coleman et al. | |
| 6,476,000 B1 | 11/2002 | Agrawal | |
| 6,486,186 B2 | 11/2002 | Fowler et al. | |
| 6,514,985 B1 | 2/2003 | Gerster et al. | |
| 6,518,265 B1 | 2/2003 | Kato et al. | |

(Continued)

FOREIGN PATENT DOCUMENTS

EP     0376534     7/1990
EP     0 394 026   10/1990

(Continued)

OTHER PUBLICATIONS

Garland, "Imiquimod" *Current Opinion in Infection Diseases*, 2003, vol. 16, pp. 85-89.

(Continued)

*Primary Examiner* — Sreeni Padmanabhan
*Assistant Examiner* — Kendra D Carter
(74) *Attorney, Agent, or Firm* — Medicis Pharmaceutical Corporation

(57) ABSTRACT

Methods of improving skin quality are disclosed. Generally, the methods include topically administering an IRM compound to a treatment area of skin for a period of time and in an amount effective for improving the quality of the skin. Suitable IRM compound compounds include agonists of one or more TLRs.

8 Claims, No Drawings

U.S. PATENT DOCUMENTS

| | | |
|---|---|---|
| 6,518,280 B2 | 2/2003 | Gerster et al. |
| 6,525,028 B1 | 2/2003 | Johnson et al. |
| 6,525,064 B1 | 2/2003 | Dellaria et al. |
| 6,528,086 B2 | 3/2003 | Zhang |
| 6,541,485 B1 | 4/2003 | Crooks et al. |
| 6,545,016 B1 | 4/2003 | Dellaria et al. |
| 6,545,017 B1 | 4/2003 | Dellaria et al. |
| 6,558,951 B1 | 5/2003 | Tomai et al. |
| 6,573,273 B1 | 6/2003 | Crooks et al. |
| 6,649,172 B2 | 11/2003 | Johnson |
| 6,656,938 B2 | 12/2003 | Crooks et al. |
| 6,660,735 B2 | 12/2003 | Crooks et al. |
| 6,660,747 B2 | 12/2003 | Crooks et al. |
| 6,664,260 B2 | 12/2003 | Charles et al. |
| 6,664,264 B2 | 12/2003 | Dellaria et al. |
| 6,664,265 B2 | 12/2003 | Crooks et al. |
| 6,667,312 B2 | 12/2003 | Bonk et al. |
| 6,670,372 B2 | 12/2003 | Charles et al. |
| 6,677,347 B2 | 1/2004 | Crooks et al. |
| 6,677,348 B2 | 1/2004 | Heppner et al. |
| 6,677,349 B1 | 1/2004 | Griesgraber |
| 6,683,088 B2 | 1/2004 | Crooks et al. |
| 6,706,728 B2 | 3/2004 | Hedenstrom et al. |
| 6,743,920 B2 | 6/2004 | Lindstrom et al. |
| 6,756,382 B2 | 6/2004 | Coleman et al. |
| 6,818,650 B2 | 11/2004 | Griesgraber |
| 6,825,350 B2 | 11/2004 | Crooks et al. |
| 2002/0016332 A1 | 2/2002 | Slade |
| 2002/0055517 A1 | 5/2002 | Smith |
| 2002/0058674 A1 | 5/2002 | Hedenstrom et al. |
| 2002/0110840 A1 | 8/2002 | Tomai et al. |
| 2003/0022302 A1 | 1/2003 | Lewis et al. |
| 2003/0072724 A1* | 4/2003 | Maibach et al. ............... 424/59 |
| 2003/0133913 A1 | 7/2003 | Tomai et al. |
| 2003/0139364 A1 | 7/2003 | Krieg et al. |
| 2003/0144283 A1 | 7/2003 | Coleman et al. |
| 2003/0161797 A1 | 8/2003 | Miller et al. |
| 2003/0199461 A1 | 10/2003 | Averett et al. |
| 2003/0199538 A1 | 10/2003 | Skwierczynski et al. |
| 2004/0010007 A1 | 1/2004 | Dellaria et al. |
| 2004/0014779 A1 | 1/2004 | Gorden et al. |
| 2004/0023870 A1 | 2/2004 | Dedera et al. |
| 2004/0087614 A1 | 5/2004 | Baumann et al. |
| 2004/0091491 A1 | 5/2004 | Kedl et al. |
| 2004/0132079 A1 | 7/2004 | Gupta et al. |
| 2004/0180919 A1 | 9/2004 | Miller et al. |
| 2004/0248837 A1* | 12/2004 | Raz et al. ..................... 514/44 |
| 2009/0232755 A1 | 9/2009 | Baumann |

FOREIGN PATENT DOCUMENTS

| | | |
|---|---|---|
| EP | 1 104 764 A1 | 6/2001 |
| EP | 1427445 | 6/2004 |
| JP | 7-501540 | 2/1995 |
| JP | 9-208584 | 8/1997 |
| JP | 63-135324 | 6/1998 |
| JP | 11-80156 | 3/1999 |
| JP | 11-222432 | 8/1999 |
| JP | 2000-247884 | 9/2000 |
| JP | 2001-322932 | 11/2001 |
| JP | 2002-193796 | 7/2002 |
| WO | WO 98/17279 | 4/1998 |
| WO | WO 00/47719 A2 | 8/2000 |
| WO | WO 00/75304 A1 | 12/2000 |
| WO | WO 00/76505 A1 | 12/2000 |
| WO | WO 00/76518 A1 | 12/2000 |
| WO | WO 01/74343 A2 | 10/2001 |
| WO | WO 02/08595 | 1/2002 |
| WO | WO 02/36592 A1 | 5/2002 |
| WO | WO 02/46188 A2 | 6/2002 |
| WO | WO 02/46189 A2 | 6/2002 |
| WO | WO 02/46190 A2 | 6/2002 |
| WO | WO 02/46191 A2 | 6/2002 |
| WO | WO 02/46192 A2 | 6/2002 |
| WO | WO 02/46193 A2 | 6/2002 |
| WO | WO 02/46194 A2 | 6/2002 |
| WO | WO 02/46749 A2 | 6/2002 |
| WO | WO 02/085905 A1 | 10/2002 |
| WO | WO 02/102377 A1 | 12/2002 |
| WO | WO 03/020889 A2 | 3/2003 |
| WO | WO 03/043572 A2 | 5/2003 |
| WO | WO 03/045338 | 6/2003 |
| WO | WO 03/045391 A1 | 6/2003 |
| WO | WO 03/089602 | 10/2003 |
| WO | WO 03/103584 A2 | 12/2003 |

OTHER PUBLICATIONS

Gorden et al., "Synthetic TLR Agonists Reveal Functional Differences between Human TLR7 and TLR8", *The Journal of Immunology*, 2005, vol. 174, pp. 1259-1268.

Sauder et al., "Randomized, Single-Blind, Placebo-Controlled Study of Topical Application of the Immune Response Modulator Resiquimod in Healthy Adults", *Antimicrobial Agents and Chemotherapy*, Dec. 2003, vol. 47, No. 12, pp. 3846-3852.

Akira S. et al., "Recognition of pathogen-associated molecular patterns by TLR family", *Immunology Letters*, 2003, vol. 85, pp. 85-95.

Ozinsky A. et al., "The repertoire for pattern recognition of pathogens by the innate immune system is defined by cooperation between Toll-like receptors", *Proc. Nat. Acad. Sci.*, Dec. 2000, vol. 97, No. 25, pp. 13766-13771.

Testerman, et al., "Cytokine Induction by the Immunomodulators Imiquimod and S-27609", *Journal of Leukocyte Biology*, vol. 58, pp. 365-372, Sep. 1995.

Chollet, et al, "Development of a Topically Active Imiquimod Formulation" *Pharmaceutical Development and Technology*, 4(1), pp. 35-43 (1999)

Brassard et al.; "Interferon-α as an immunotherapeutic protein"; Journal of Leukocyte Biology; vol. 71; Apr. 2002; pp. 565-581.

Izumi et al.; "1*H*-imidazo[4,5-*c*]quinoline Derivatives as Novel Potent TNF-α Suppressors: Synthesis and Structure-Activity Relationship of 1-, 2-and 4-Substituted 1*H*-imidazo[4,5-*c*]quinolines or 1*H*-imidazo[4,5-*c*]pyridines"; *Bioorganic and Medicinal Chemistry*, vol. 11, pp. 2541-2550 2003.

Hornung et al., "Quantitative Expression of Toll-Like Receptor 1-10 mRNA in Cellular Subsets of Human Peripheral Blood Mononuclear Cells and Sensitivity to CpG Oligodeoxyncieotides[1]", *The Journal of Immunology*, 2002, 168; pp. 4531-4537.

Hemmi et al., "Small anti-viral compounds activate immune cells via the TLR7 MyD88-dependent Signaling pathway", *Nature Immunology*, vol. 3, No. 2; Feb. 2002; pp. 196-200.

Medzhitov, "Toll-Like Receptors and Innate Immunity", *Nature Reviews Immunology*, vol. 1; Nov. 2001, pp. 135-145.

Jurk et al. "Human TLR7 and TLR8 independently confer responsiveness to the antiviral compound R-848", *Nature Immunology*, Jun. 2002, vol. 3, No. 6; p. 1.

Akira et al., "Toll-like receptors: critical proteins linking innate and acquired immunity" *Nature Immunology*, Aug. 2001, vol. 2, No. 8; pp. 675-680

Heil et al.; "Synthetic immunostimulatory compounds activate immune cells via TLR7 and TLR8"; 33th Annual Meeting of the Deutsche Gessellschaft für Immunologie, Marburg 2002—Abstract C.6.

Barland, Chantel O., et al., Journal of Investigative Dermatology, "Imiquimod-Induced Interleukin-1" Stimulation Improves Barrier Homeostasis in Aged Murine Epidermis, 2004, pp. 330-336.

Gibson et al., *Cell Immunol*. 218(1-2):74-86 (2002).

Salasche, et al., Cycle Therapy of Actinic Keratoses of the Face and Scalp with 5% Topical Imiquimod Cream: An Open-Label Trial, *Am Acad Dermatol*, Oct. 2002, pp. 571-577.

Stanley, Imiquimod and the Imidazoquinolones: Mechanism of Action and Therapeutic Potential, 2002 Blackwell Science Ltd., Clinical and Experimental Dermatology, vol. 27, pp. 571-577.

\* cited by examiner

METHODS OF IMPROVING SKIN QUALITY

CROSS-REFERENCE TO RELATED APPLICATION

This application claims priority to U.S. Provisional Patent Application No. 60/454,245, filed Mar. 13, 2003.

BACKGROUND OF THE INVENTION

Skin condition is continuously affected by various factors including, for example, humidity, UV-light, cosmetics, aging, diseases, stress, cigarette smoking, and eating habits, each of which can result in various skin changes. Additionally, certain changes appear on the skin that are characteristic of aging, many of which are reflected, in particular, by a change in the skin's structure. The main clinical signs of aging of the skin are, in particular, the appearance of fine lines and deep wrinkles, each of which can increase with age. Wrinkles can be caused by both the chronological aging of the skin and photoaging of skin due to exposure of the skin to sunlight, UV-radiation and other forms of actinic radiation.

In young skin, the collagen just beneath the surface of the skin forms an organized lattice with good elasticity and flexibility. During aging, the collagen structure can change, thus causing changes in the cosmetic appearance of the skin that many find undesirable. Current methods of improving skin quality include the application of cosmetic products containing active agents such as moisturizers, alpha-hydroxy acids, beta-hydroxy acids and retinoids. However, other methods are still sought after.

SUMMARY OF THE INVENTION

It has been found that certain immune response modifier (IRM) compounds can be used to improve skin quality.

In some aspects, the present invention provides methods of improving skin quality by topically applying to the skin an IRM compound in an amount effective to improve the quality of the skin.

In some aspects, the present invention provides methods of visibly reducing a skin change associated with aging by topically applying to skin exhibiting an age-associated change an IRM compound, wherein the IRM compound is applied in an amount and for a period of time sufficient to visibly reduce the skin change associated with aging.

In other aspects, the present invention includes methods of visibly reducing a human skin wrinkle by topically applying to the human skin wrinkle an IRM compound in an amount and for a period of time sufficient to visibly reduce the wrinkle.

In other aspects, the present invention includes methods of treating aging related skin conditions by topically applying to the skin an IRM compound for a period of time and in an amount sufficient to effect changes in the dermis.

In still other aspects, the present invention includes methods for reducing the appearance of skin changes associated with aging by topically applying to an area of skin exhibiting skin changes associated with aging an IRM compound in an amount and for a period of time sufficient to reduce the appearance of skin changes associated with aging.

In yet other aspects, the present invention includes methods for improving the quality of facial skin by topically applying to the facial skin an IRM compound in an amount and for a period of time sufficient to reverse or prevent changes in the dermis, where the changes in the dermis result from natural or innate aging or exposure to actinic radiation, and the changes in the dermis include diminution in the number and diameter of elastic fibers in the papillary dermis, atrophy of the dermis, reduction in subcutaneous adipose tissue, deposition of abnormal elastic materials in the upper dermis, and combination thereof.

In some embodiments of the methods of the present invention, the IRM compound may be an agonist of at least one TLR; including an agonist of TLR7, TLR8 or both TR7 and TR8.

In some embodiments of the methods of the present invention, the IRM compound may be administered via a topical application vehicle including a cream, a foam, a gel, a spray, an ointment, a lotion, a solution, a suspension, a dispersion, an emulsion, a microemulsion, a paste, a powder, a wipe, or an oil.

In the some embodiments of the methods of the present invention, the IRM compound may be an imidazoquinoline amine, a tetrahydroimidazoquinoline amine, an imidazopyridine amine, a 1,2-bridged imidazoquinoline amine, a 6,7-fused cycloalkylimidazopyridine amine, an imidazonaphthyridine amine, a tetrahydroimidazonaphthyridine amine, an oxazoloquinoline amine, a thiazoloquinoline amine, an oxazolopyridine amine, a thiazolopyridine amine, an oxazolonaphthyridine amine, or a thiazolonaphthyridine amine, or a combination thereof.

Various other features and advantages of the present invention should become readily apparent with reference to the following detailed description, examples, and claims. In several places throughout the specification, guidance is provided through lists of examples. In each instance, the recited list serves only as a representative group and should not be interpreted as an exclusive list.

DETAILED DESCRIPTION OF ILLUSTRATIVE EMBODIMENTS OF THE INVENTION

The present invention provides methods of improving skin quality by the topical administration of an immune response modifier (IRM) compound to the skin in an amount effective to improve the quality of skin.

IRM compounds have previously been shown to be useful for treating many different types of conditions. It has now been found that when topically applied to the skin such as, for example, to treat a dermatological condition, certain IRM compounds provide a secondary benefit of improving the quality of skin treated with the IRM. That is, treatment of skin with an IRM compound not only, for example, clears lesions associated with the condition being treated, but also leaves the treated skin in even better condition than skin unaffected by the condition and, therefore, left untreated.

IRM compounds include compounds that possess potent immunomodulating activity including but not limited to antiviral and antitumor activity. Certain IRMs modulate the production and secretion of cytokines. For example, certain IRM compounds induce the production and secretion of cytokines such as, e.g., Type I interferons, TNF-α, IL-1, IL-6, IL-8, IL-10, IL-12, MIP-1, and/or MCP-1. As another example, certain IRM compounds can inhibit production and secretion of certain TH2 cytokines, such as IL-4 and IL-5. Additionally, some IRM compounds are said to suppress IL-1 and TNF (U.S. Pat. No. 6,518,265).

Certain IRMs are small organic molecules (e.g., molecular weight under about 1000 Daltons, preferably under about 500 Daltons, as opposed to large biological molecules such as proteins, peptides, and the like) such as those disclosed in, for example, U.S. Pat. Nos. 4,689,338; 4,929,624; 4,988,815; 5,037,986; 5,175,296; 5,238,944; 5,266,575; 5,268,376;

5,346,905; 5,352,784; 5,367,076; 5,389,640; 5,395,937; 5,446,153; 5,482,936; 5,693,811; 5,741,908; 5,756,747; 5,939,090; 6,039,969; 6,083,505; 6,110,929; 6,194,425; 6,245,776; 6,331,539; 6,376,669; 6,451,810; 6,525,064; 6,541,485; 6,545,016; 6,545,017; 6,558,951; 6,573,273; 6,656,938; 6,660,735; 6,660,747; 6,664,260; 6,664,264; 6,664,265; 6,667,312; 6,670,372; 6,677,347; 6,677,348; 6,677,349; 6,683,088; European Patent 0 394 026; U.S. Patent Publication Nos. 2002/0016332; 2002/0055517; 2002/0110840; 2003/0133913; 2003/0199538; and 2004/0014779; and International Patent Publication Nos. WO 01/74343; WO 02/46749 WO 02/102377; WO 03/020889; WO 03/043572; WO 03/045391; and WO 03/103584.

Additional examples of small molecule IRMs include certain purine derivatives (such as those described in U.S. Pat. No. 6,376,501, and 6,028,076), certain imidazoquinoline amide derivatives (such as those described in U.S. Pat. No. 6,069,149), certain imidazopyridine derivatives (such as those described in U.S. Pat. No. 6,518,265), certain benzimidazole derivatives (such as those described in U.S. Pat. No. 6,387,938), certain derivatives of a 4-aminopyrimidine fused to a five membered nitrogen containing heterocyclic ring (such as adenine derivatives described in U.S. Pat. Nos. 6,376,501; 6,028,076 and 6,329,381; and in WO 02/08595), and certain 3-β-D-ribofuranosylthiazolo[4,5-d]pyrimidine derivatives (such as those described in U.S. Publication No. 2003/0199461).

Other IRMs include large biological molecules such as oligonucleotide sequences. Some IRM oligonucleotide sequences contain cytosine-guanine dinucleotides (CpG) and are described, for example, in U.S. Pat. Nos. 6,194,388; 6,207,646; 6,239,116; 6,339,068; and 6,406,705. Some CpG-containing oligonucleotides can include synthetic immunomodulatory structural motifs such as those described, for example, in U.S. Pat. Nos. 6,426,334 and 6,476,000. Other IRM nucleotide sequences lack CpG sequences and are described, for example, in International Patent Publication No. WO 00/75304.

Other IRMs include biological molecules such as aminoalkyl glucosaminide phosphates (AGPs) and are described, for example, in U.S. Pat. Nos. 6,113,918; 6,303,347; 6,525,028; and 6,649,172.

Certain IRMs can function as Toll-like receptor (TLR) agonists, i.e., their immunomodulating influence is exerted through a TLR-mediated cellular pathway. For example, some small molecule IRMs have been identified as agonists of one or more members of the TLR receptor family, TLR2, TLR4, TLR6, TLR7, and TLR8; certain AGPS have been identified as agonists of TLR4; and, certain CpGs have been identified as a agonists of TLR9. In many cases, activating a TLR-mediated pathway results in gene transcription, cytokine or co-stimulatory marker expression regardless of the particular TLR that is activated.

In certain embodiments of the present invention, the IRM is an agonist of at least one TLR. In particular embodiments, the IRM compound can be an agonist of TLR7, TLR8, and/or TLR9. In alternative embodiments, the IRM compound is an agonist of TLR4. In certain specific embodiments, the IRM is an agonist of TLR8 or an agonist of both TLR7 and TLR8. The IRM may induce the production of one or more cytokines, including but not limited to Type I interferons, TNF-α, IL-10, and IL-12. See, for example, Gibson et al., *Cell Immunol.* 218(1-2):74-86 (2002). The IRM may effect the maturation, activation, and/or migration of cells of the myeloid lineage, including, but not limited to, macrophages, dendritic cells, and Langerhans cells.

Suitable IRM compounds include, but are not limited to, the small molecule IRM compounds described above having a 2-aminopyridine fused to a five membered nitrogen-containing heterocyclic ring. Such compounds include, for example, imidazoquinoline amines including but not limited to amide substituted imidazoquinoline amines, sulfonamide substituted imidazoquinoline amines, urea substituted imidazoquinoline amines, aryl ether substituted imidazoquinoline amines, heterocyclic ether substituted imidazoquinoline amines, amido ether substituted imidazoquinoline amines, sulfonamido ether substituted imidazoquinoline amines, urea substituted imidazoquinoline ethers, thioether substituted imidazoquinoline amines, and 6-, 7-, 8-, or 9-aryl or heteroaryl substituted imidazoquinoline amines; tetrahydroimidazoquinoline amines including but not limited to amide substituted tetrahydroimidazoquinoline amines, sulfonamide substituted tetrahydroimidazoquinoline amines, urea substituted tetrahydroimidazoquinoline amines, aryl ether substituted tetrahydroimidazoquinoline amines, heterocyclic ether substituted tetrahydroimidazoquinoline amines, amido ether substituted tetrahydroimidazoquinoline amines, sulfonamido ether substituted tetrahydroimidazoquinoline amines, urea substituted tetrahydroimidazoquinoline ethers, and thioether substituted tetrahydroimidazoquinoline amines; imidazopyridine amines including but not limited to amide substituted imidazopyridine amines, sulfonamido substituted imidazopyridine amines, urea substituted imidazopyridine amines, aryl ether substituted imidazopyridine amines, heterocyclic ether substituted imidazopyridine amines, amido ether substituted imidazopyridine amines, sulfonamido ether substituted imidazopyridine amines, urea substituted imidazopyridine ethers, and thioether substituted imidazopyridine amines; 1,2-bridged imidazoquinoline amines; 6,7-fused cycloalkylimidazopyridine amines; imidazonaphthyridine amines; tetrahydroimidazonaphthyridine amines; oxazoloquinoline amines; thiazoloquinoline amines; oxazolopyridine amines; thiazolopyridine amines; oxazolonaphthyridine amines; thiazolonaphthyridine amines; and 1H-imidazo dimers fused to pyridine amines, quinoline amines, tetrahydroquinoline amines, naphthyridine amines, or tetrahydronaphthyridine amines. Various combinations of IRMs can be used if desired.

In some embodiments, the IRM compound is an imidazoquinoline amine such as, for example, 1-(2-methylpropyl)-1H-imidazo[4,5-c]quinolin-4-amine or 4-amino-α,α-dimethyl-2-ethoxymethyl-1H-imidazo[4,5-c]quinolin-1-ethanol. In one particular embodiment, the IRM compound is 1-(2-methylpropyl)-1H-imidazo[4,5-c]quinolin-4-amine.

In an alternative embodiment, the IRM compound is an imidazonaphthyridine amine such as, for example, 2-methyl-1-(2-methylpropyl)-1H-imidazo[4,5-c][1,5]naphthyridin-4-amine or 1-(2-methylpropyl)-1H-imidazo[4,5-c][1,5]naphthyridin-4-amine.

In another alternative embodiment, the IRM compound is a sulfonamide substituted imidazoquinoline amine such as, for example, N-[4-(4-amino-2-ethyl-1H-imidazo[4,5-c]quinolin-1-yl)butyl]methanesulfonamide.

In another alternative embodiment, the IRM compound is an amide substituted imidazoquinoline amine such as, for example, N-{2-[4-amino-2-(ethoxymethyl)-1H-imidazo[4,5-c]quinolin-1-yl]-1,1-dimethylethyl} cyclohexanecarboxamide.

In another alternative embodiment, the IRM compound is a thioether substituted imidazoquinoline amine such as, for example, 2-butyl-1-[2-(propylsulfonyl)ethyl]-1H-imidazo[4,5-c]quinolin-4-amine.

In yet another alternative embodiment, the IRM compound is an imidazopyridine amine such as, for example, N-{2-[4-amino-2-(ethoxymethyl)-6,7-dimethyl-1H-imidazo[4,5-c]pyridin-1-yl]ethyl}benzamide.

In certain embodiments, the IRM compound may be an imidazonaphthyridine amine, a tetrahydroimidazonaphthyridine amine, an oxazoloquinoline amine, a thiazoloquinoline amine, an oxazolopyridine amine, a thiazolopyridine amine, an oxazolonaphthyridine amine, or a thiazolonaphthyridine amine.

In certain embodiments, the IRM compound may be a substituted imidazoquinoline amine, a tetrahydroimidazoquinoline amine, an imidazopyridine amine, a 1,2-bridged imidazoquinoline amine, a 6,7-fused cycloalkylimidazopyridine amine, an imidazonaphthyridine amine, a tetrahydroimidazonaphthyridine amine, an oxazoloquinoline amine, a thiazoloquinoline amine, an oxazolopyridine amine, a thiazolopyridine amine, an oxazolonaphthyridine amine, or a thiazolonaphthyridine amine.

As used herein, a substituted imidazoquinoline amine refers to an amide substituted imidazoquinoline amine, a sulfonamide substituted imidazoquinoline amine, a urea substituted imidazoquinoline amine, an aryl ether substituted imidazoquinoline amine, a heterocyclic ether substituted imidazoquinoline amine, an amido ether substituted imidazoquinoline amine, a sulfonamido ether substituted imidazoquinoline amine, a urea substituted imidazoquinoline ether, a thioether substituted imidazoquinoline amine, or a 6-, 7-, 8-, or 9-aryl or heteroaryl substituted imidazoquinoline amine. As used herein, substituted imidazoquinoline amines specifically and expressly exclude 1-(2-methylpropyl)-1H-imidazo[4,5-c]quinolin-4-amine and 4-amino-α,α-dimethyl-2-ethoxymethyl-1H-imidazo[4,5-c]quinolin-1-ethanol.

Unless otherwise indicated, reference to a compound can include the compound in any pharmaceutically acceptable form, including any isomer (e.g., diastereomer or enantiomer), salt, solvate, polymorph, and the like. In particular, if a compound is optically active, reference to the compound can include each of the compound's enantiomers as well as racemic mixtures of the enantiomers.

An IRM compound may be provided in any formulation suitable for administration to a subject. Suitable types of formulations are described, for example, in U.S. Pat. Nos. 5,736,553; 5,238,944; 5,939,090; 6,365,166; 6,245,776; 6,486,186; European Patent No. EP 0 394 026; and U.S. Patent Publication No. 2003/0199538. The compound may be provided in any suitable form including but not limited to a solution, a suspension, an emulsion, or any form of mixture. The compound may be delivered in formulation with any pharmaceutically acceptable excipient, carrier, or vehicle. For example, the formulation may be delivered in a conventional topical dosage form such as, for example, a cream, an ointment, an aerosol formulation, a non-aerosol spray, a gel, a foam, a solution, a suspension, a dispersion, an emulsion, a microemulsion, a paste, a powder, a solid stick (e.g., wax- or petroleum-based sticks), a wipe, an oil, a lotion, and the like. In one particular embodiment, the IRM compound is provided in a cream formulation suitable for topical administration.

A formulation suitable for practicing the invention may include one or more additional active ingredients such as, for example, another IRM compound, acyclovir, valcyclovir, pencyclovir, amphotericins, chlorhexidine, clotrimazole, ketoconazole, econazole, miconazole, metronidazole, minocycline, nystatin, neomycin, kanamycin, phenytoin, octyl dimethyl PABA, octyl methoxycinnamate, PABA and other esters, octyl salicylate, oxybenzone, dioxybenzone, tocopherol, tocopheryl acetate, selenium sulfide, zinc pyrithione, soluble elastin, diphenhydramine, pramoxine, lidocaine, procaine, erythromycin, tetracycline, clindamycin, crotamiton, hydroquinone and its monomethyl and benzyl ethers, naproxen, ibuprofen, cromolyn, retinoic acid, retinol, retinyl palmitate, retinyl acetate, coal tar, griseofulvin, hydrocortisone, hydrocortisone 21-acetate, hydrocortisone 17-valerate, hydrocortisone 17-butyrate, betamethasone valerate, betamethasone dipropionate, triamcinolone acetonide, fluocinonide, clobetasol propionate, minoxidil, dipyridamole, diphenylhydantoin, benzoyl peroxide, 5-fluorouracil, vitamin A acetate (retinyl acetate) and vitamin E acetate (tocopheryl acetate). In some embodiments, additional beneficial effects may also be found when a skin-bleaching agent, such as a hydroquinone (including glycolic acid, lactic acid, methyllactic acid, mandelic acid, pyruvic acid, methyl pyruvate, ethyl pyruvate, benzilic acid, gluconolactone, malic acid, tartaric acid, citric acid, and tropic acid) or a monobenzone, is incorporated into an IRM composition. In some embodiments, the IRM compound may be incorporated into, for example, a sunscreen, a skin lotion, a skin moisturizer, or other cosmetic.

The composition of a suitable formulation may depend at least in part on many factors known in the art including but not limited to the physical and chemical nature of the IRM compound; the nature of the carrier; the dosing regimen; the state of the subject's immune system (e.g., suppressed, compromised, stimulated); the method of administering the IRM compound; and the desired result (e.g., wrinkle reduction, hydration, scar prevention, etc.). Accordingly it is not practical to set forth generally a single formulation suitable for improving skin quality for all possible applications. Those of ordinary skill in the art, however, can readily determine a suitable formulation with due consideration of such factors.

A suitable formulation may contain, for example, about 0.001%, about 0.002%, about 0.005%, about 0.01%, about 0.015%, about 0.02%, about 0.025%, about 0.05%, about 0.1%, about 0.25%, about 0.5%, about 0.75%, about 1%, about 2.5%, about 5%, about 7.5%, about 10%, about 25%, or about 50% active IRM compound. In one particular embodiment, the composition includes about 5% IRM compound.

Skin treated by practicing the invention can include facial skin, skin on the neck, hands, arms, legs, or torso, and skin of other body regions.

Improving skin quality includes reversing, slowing the progression of, or preventing skin changes associated with natural or innate aging. As used herein, "prevent" and variations thereof refer to any degree of delaying the onset of skin changes. For example, improving skin quality includes the reversal, slowing the progression of, or prevention of skin changes associated with sun damage or photoaging—i.e., skin changes associated with exposure to sunlight or other forms of actinic radiation (for example, such as UV radiation and tanning booths). As another example, improving skin quality also can include reversing, slowing the progression of, or preventing skin changes resulting from extrinsic factors, including, but not limited to, radiation, air pollution, wind, cold, dampness, heat, chemicals, smoke, cigarette smoking, and combinations thereof.

Improving skin quality also can include reversing, preventing or reducing scarring the can result, for example, from certain skin conditions (e.g., acne), infections (i.e., leishmaniasis), or injury (e.g., abrasions, punctures, lacerations, or surgical wounds).

Skin changes treatable by practicing the invention include, for example, wrinkles (including, but not limited to, human facial wrinkles), deepening of skin lines, thinning of skin, reduced scarring, yellowing of the skin, mottling, hyperpigmentation, appearance of pigmented and/or non-pigmented age spots, leatheriness, loss of elasticity, loss of recoilability, loss of collagen fibers, abnormal changes in the elastic fibers, deterioration of small blood vessels of the dermis, formation of spider veins, and combinations thereof.

Skin changes in the dermis also can be treated by practicing the invention. Such changes in the dermis include, but are not limited to, a reduction in the number and diameter of elastic fibers in the papillary dermis, atrophy of the dermis, reduction in subcutaneous adipose tissue, deposition of abnormal elastic materials in the upper dermis, and combinations thereof.

Improving skin quality includes decreasing, reducing, and/or minimizing one or more of the skin changes discussed above. Improving skin quality may result in the skin having a more youthful appearance. Improving skin quality may result in the skin having a smoother, hydrated (i.e., less dry), or less scaly appearance.

In some embodiments, an IRM compound may be administered to treat—i.e., reverse or slow the progression of—one or more skin changes. Thus, the IRM compound may be administered after one or more skin changes have occurred. In other embodiments, an IRM compound may be administered to prevent one or more skin changes. Thus, the IRM compound may be administered before one or more skin changes have occurred, to prevent or slow the onset of such skin changes.

For example, in certain embodiments, improving skin quality can include a reduction in roughness, dryness, or scaliness. Skin quality assessments, performed in conjunction with efficacy trials in which cancerous (basal cell carcinoma, BCC) or pre-cancerous (actinic keratosis, AK) dermal lesions were treated with an IRM compound (5% imiquimod cream ALDARA, 3M Pharmaceuticals) indicate that treatment with the IRM compound not only cleared the lesions, but also improved skin quality of the treated area.

The IRM compound was administered once daily either 5× per week or 7× per week for six weeks for treating BCC. Subjects in each treatment group completed both an initiation (prior to the 6-week treatment period) skin surface assessment and a follow-up (twelve weeks after completion of the treatment period) skin surface assessment. Skin quality was assessed on a scale of 1 (none) to 4 (severe). The assessment from the initiation visit established a baseline against which the follow-up assessment was compared. Both of the IRM-treated groups (5× per week and 7× per week) showed a substantial decrease in the degree of rough/dry/scaly skin surface over the treatment area. The results (see Table 1) were statistically significant over the baseline as well as statistically significant over the placebo-treated control group.

In a separate study, the IRM was administered once daily either 2× per week or 3× per week for sixteen weeks for treating AK. Subjects in each treatment group completed both an initiation (prior to the 16-week treatment period) skin surface assessment and a follow-up (eight weeks after completion of the treatment period) skin surface assessment. Skin quality was assessed on a scale of 1 (none) to 4 (severe). The assessment from the initiation visit established a baseline against which the follow-up assessment was compared. Both of the IRM-treated groups (2× per week and 3× per week) showed a substantial decrease in the degree of rough/dry/scaly skin surface over the treatment area. The results (see Table 2) for both groups were statistically significant against both the baseline assessments and the placebo-treated control group.

The particular amount of IRM compound necessary to improve skin quality may depend, at least in part, on one or more factors. Such factors include, but are not limited to, the particular IRM compound being administered; the state of the subject's overall health; the state of the subject's immune system (e.g., suppressed, compromised, stimulated); the route of administering the IRM; and the desired result (e.g., wrinkle reduction, reducing dryness, etc.). Accordingly, it is not practical to set forth generally the amount that constitutes an amount of an IRM compound effective for improving skin quality. Those of ordinary skill in the art, however, can readily determine the appropriate amount with due consideration of such factors.

In some embodiments, the methods of the present invention include administering sufficient IRM compound to provide a dose of, for example, from about 100 ng/kg to about 50 mg/kg to the subject, although in some embodiments the method may be performed by administering IRM compound in a dose outside this range. In some of these embodiments, the method includes administering sufficient IRM compound to provide a dose of from about 10 µg/kg to about 5 mg/kg to the subject, for example, a dose of from about 100 µg/kg to about 1 mg/kg.

The dosing regimen may depend at least in part on many factors known in the art such as, for example, the physical and chemical nature of the IRM compound; the nature of the carrier; the amount of IRM being administered; the period over which the IRM compound is being administered; the state of the subject's immune system (e.g., suppressed, compromised, stimulated); the method of administering the IRM compound; and the desired result. Accordingly it is not practical to set forth generally the dosing regimen effective for improving skin quality for all possible applications. Those of ordinary skill in the art, however, can readily determine an appropriate dosing regimen with due consideration of such factors.

In some embodiments of the invention, the IRM compound may be administered, for example, from a single dose to multiple doses administered multiple times per day. In certain embodiments, the IRM compound may be administered from about once per week to about once per day. In one particular embodiment, the IRM compound is administered once per day, two days per week. In an alternative embodiment, the IRM compound is administered once per day, three times per week. In another alternative embodiment, the IRM compound is administered one per day, five days per week. In yet another alternative embodiment, the IRM compound is administered once per day, seven days per week.

The period of time that is sufficient for practicing the invention may depend, at least in part, on factors such as, for example, the physical and chemical nature of the IRM compound; the nature of the carrier; the amount of IRM being administered; the frequency with which the IRM compound is being administered; the state of the subject's immune system (e.g., suppressed, compromised, stimulated); the method of administering the IRM compound; and the desired result. Accordingly it is not practical to set forth generally the period of time necessary to improve skin quality for all possible applications. Those of ordinary skill in the art, however, can readily determine an appropriate period of time with due consideration of such factors.

In some embodiments, a sufficient period of time may range from at least one day to about six months, although in some embodiments the invention may be practiced by administering IRM compound for a period outside this range. In some embodiments, the IRM compound may be administered for at least one week. In an alternative embodiment, the IRM compound may be administered for at least about four weeks. In another alternative embodiment, the IRM compound may be administered for at least about eight weeks. In another alternative embodiment, the IRM compound may be administered for at least about sixteen weeks.

The methods of the present invention may be performed on any suitable subject. Suitable subjects include, but are not limited to, animals such as, but not limited to, humans, non-human primates, rodents, dogs, cats, horses, pigs, sheep, goats, or cows.

EXAMPLES

The following examples have been selected merely to further illustrate features, advantages, and other details of the invention. It is to be expressly understood, however, that while the examples serve this purpose, the particular materials and amounts used as well as other conditions and details are not to be construed in a matter that would unduly limit the scope of this invention. Unless otherwise indicated, all percentages and ratios are by weight.

Example 1

Treatment of Rough, Dry, or Scaly Skin

Volunteer subjects with superficial basal cell carcinoma (BCC) were randomized to either the 5% imiquimod cream formulation (ALDARA, 3M Pharmaceuticals, St. Paul, Minn.) or a placebo cream (Vehicle) in one of two treatment regimens: (1) once daily for seven days per week (7×/week), and (2) once daily for five consecutive days per week and no treatment for the remaining two days (5×/week). Subjects in each group received treatment for six weeks.

Subjects were instructed to administer a single application of cream (Vehicle or 5% imiquimod, as assigned) to a target tumor just prior to normal sleeping hours according to the dosing regimen to which they were assigned. The subjects were instructed to wash the tumor lesion prior to applying the cream, and then rub the cream into the tumor and into extramarginal skin about 1 cm around the tumor. The subjects were instructed to leave the cream in place for at least eight hours without occlusion.

Subjects completed interval visits 1, 3, and 6 weeks after treatment was initiated and at twelve weeks after the end of treatment. At the 12-weeks post-treatment visit, the treatment area was clinically and histologically evaluated for evidence of BCC.

In addition, the treatment area was evaluated for skin quality. Skin quality was assessed on a scale of 1 (none) to 4 (severe). The assessment from the Initiation visit established a baseline against which the Follow-up assessment was compared. Both IRM-treated groups (5× per week and 7× per week) showed a substantial decrease in the degree of rough/dry/scaly skin surface over the treatment area. The results were statistically significant over the baseline as well as statistically significant over the placebo-treated control group. Results are shown in Table 1.

TABLE 1

| Treatment | Visit | N = | None | Mild | Moderate | Severe |
|---|---|---|---|---|---|---|
| IRM 5× | Initiation | 185 | 76 (41%) | 93 (50%) | 16 (9%) | 0 (0%) |
| | Follow-up | 178 | 141 (79%) | 36 (20%) | 1 (1%) | 0 (0%) |
| Vehicle 5× | Initiation | 178 | 53 (30%) | 105 (59%) | 20 (11%) | 0 (0%) |
| | Follow-up | 173 | 82 (47%) | 82 (47%) | 8 (5%) | 1 (1%) |
| IRM 7× | Initiation | 179 | 66 (36%) | 96 (54%) | 16 (9%) | 1 (1%) |
| | Follow-up | 168 | 139 (83%) | 27 (16%) | 2 (1%) | 0 (0%) |

TABLE 1-continued

| Treatment | Visit | N = | None | Mild | Moderate | Severe |
|---|---|---|---|---|---|---|
| Vehicle 7× | Initiation | 181 | 56 (31%) | 106 (59%) | 19 (10%) | 0 (0%) |
| | Follow-up | 169 | 88 (52%) | 73 (43%) | 7 (4%) | 1 (1%) |

Separately, volunteer subjects with actinic keratoses (AK) were randomized to either the 5% imiquimod cream formulation (ALDARA, 3M Pharmaceuticals, St. Paul, Minn.) or a placebo cream (Vehicle) in one of two treatment regimens: (1) once daily for two days per week (2×/week), and (2) once daily for three days per week (3×/week). Subjects in each group received treatment for sixteen weeks.

Subjects were instructed to administer a single application of cream (Vehicle or 5% imiquimod, as assigned) to a 25 cm$^2$ treatment area just prior to normal sleeping hours according to the dosing regimen to which they were assigned. The subjects were instructed to wash the treatment area prior to applying the cream, and then rub the cream into the treatment area. The subjects were instructed to leave the cream in place for at least eight hours without occlusion.

Subjects completed interval throughout 16-week the treatment and at eight weeks after the end of treatment. At the 8-weeks post-treatment visit, the treatment area was clinically and histologically evaluated for evidence of AK.

In addition, the treatment area was evaluated for skin quality. Skin quality was assessed on a scale of 1 (none) to 4 (severe). The assessment from the Initiation visit established a baseline against which the Follow-up assessment was compared. Both IRM-treated groups (2× per week and 3× per week) showed a substantial decrease in the degree of rough/dry/scaly skin surface over the treatment area. The results were statistically significant over the baseline as well as statistically significant over the placebo-treated control group. Results are shown in Table 2.

TABLE 2

| Treatment | Visit | N = | None | Mild | Moderate | Severe |
|---|---|---|---|---|---|---|
| IRM 2× | Initiation | 215 | 26 (12.1%) | 135 (62.8%) | 50 (23.3%) | 4 (1.9%) |
| | Follow-up | 205 | 116 (56.6%) | 76 (37.1%) | 13 (6.3%) | 0 (0%) |
| Vehicle 2× | Initiation | 221 | 33 (14.9%) | 141 (63.8%) | 44 (19.9%) | 3 (1.4%) |
| | Follow-up | 210 | 45 (21.4%) | 123 (58.6%) | 38 (18.1%) | 4 (1.9%) |
| IRM 3× | Initiation | 242 | 43 (17.8%) | 147 (60.7%) | 51 (21.1%) | 1 (0.4%) |
| | Follow-up | 226 | 132 (58.4%) | 88 (38.9%) | 6 (2.7%) | 0 (0%) |
| Vehicle 3× | Initiation | 250 | 46 (18.4%) | 144 (57.6%) | 57 (22.8%) | 3 (1.2%) |
| | Follow-up | 233 | 58 (24.9%) | 138 (59.2%) | 36 (15.5%) | 1 (0.4%) |

Example 2

Subjects having cutaneous leishmaniasis received standard care for leishmaniasis: meglumine antimonate (GLUCANTIME, Aventis Pharma, 20 mg/Kg) for 20 consecutive days. Subjects were randomized to received, in addition to the meglumine antimonate, either 5% imiquimod cream (ALDARA, 3M Pharmaceuticals, St. Paul, Minn.) or a placebo cream. A thin layer of cream was applied to each lesion every other day for 20 days (i.e., ten total applications). Doses of cream were applied by study personnel blinded to group assignments. Cream was applied with a gentle rubbing action over areas of involved but intact skin—i.e., the whole area of nodular lesions and including the periphery of ulcerative lesions (up to 0.5 cm beyond the edge of each lesion).

Treatment efficacy was evaluated at follow-up visits one, two, three, six, and twelve months after the completion of treatment. Scar quality was not an original outcome of the study and thus, no well-standardized scale for the assessment of scar quality was established. Nevertheless, study personnel blinded to group assignment throughout the treatment period and follow-up visits were able, prior to unblinding, to identify which subjects had received imiquimod during the treatment period.

Example 3

Treatment of Wrinkles

Wrinkles of skin may be due to natural aging and/or sun damage. Most fine wrinkles on the face are due to natural or innate aging, while coarse wrinkles on the face are the consequence of actinic or sun damage. Although the real mechanism of wrinkles formation in the skin is still unknown, it has been shown that visible fine wrinkles are due to diminution in the number and diameter of elastic fibers in the papillary dermis, and also due to atrophy of dermis as well as reduction in subcutaneous adipose tissue. Histopathology and electron microscopy studies indicate that coarse wrinkles are due to excessive deposition of abnormal elastic materials in the upper dermis and thickening of the skin.

A 5% cream of imiquimod, the imidazoquinoline amine 1-(2-methylpropyl)-1H-imidazo[4,5-c]quinolin-4-amine, marketed as ALDARA (3M Pharmaceuticals, St. Paul, Minn.), is provided to a randomized segment of volunteer subjects having facial wrinkles lateral and inferior to the lateral canthus. The remaining subjects receive a placebo formulation. The subjects are instructed to apply the formulation provided to them (ALDARA or placebo) at least daily on areas of facial wrinkles for 4 to 12 months. All subjects are told to avoid sun exposure, and to use sunscreen products if exposure to sunlight is unavoidable.

Evaluations are performed at the beginning of the study to establish a baseline, and at three month intervals during the study period. Evaluations include examination of the treatment area and photographing each side the subject's face. The subjects are asked not to wear any facial make-up at the time of each photographic session. Standardized photographic conditions are used. At the end of the study, clinical evaluations and review of photographs reveals substantial reductions in facial wrinkles. Clinical evaluations are performed using to the following scale:

None (0): No evidence of wrinkling.
Mild (1): Minimal evidence of wrinkles beyond lateral canthus, wrinkles are fine and shallow.
Moderate (2): Superficial wrinkles that extend beyond orbital rim, wrinkles do not fold onto each other.
Severe (3): Deep folds that extend beyond orbital rim, wrinkles begin to fold onto each other.

Evaluation scores are analyzed to establish statistical significance of changes in evaluation scores (a) over the course of the study (baseline vs. end of study), and (b) with respect to placebo (ALDARA vs. placebo). The degree of improvement and reduction in wrinkles is evaluated and determined to range from mild improvement in some subjects, to very substantial improvement in other subjects.

Example 4

Treatment of Mottled Pigmentation

Many small and large discolored lesions such as, for example, age spots (solar lentigines) develop on the face and the back of the hands with aging.

A 5% cream of imiquimod, the imidazoquinoline amine 1-(2-methylpropyl)-1H-imidazo[4,5-c]quinolin-4-amine, marketed as ALDARA (3M Pharmaceuticals, St. Paul, Minn.), is provided to a randomized segment of volunteer subjects having age spots and/or other pigmented lesions. The remaining subjects receive a placebo formulation. The subjects are instructed to apply the formulations provided to them (ALDARA or placebo) to the age spots and/or other pigmented lesions. Specific instructions are given to the subjects that the medications are to be applied at least daily to the lesions of age spots and/or other pigmented lesions.

Evaluations are performed at the beginning of the study to establish a baseline and throughout the study period. Evaluations include examination of the treatment area and photographing the treatment area. Standardized photographic conditions are used. At the end of the study, clinical evaluations and review of photographs reveals substantial reduction of irregular pigmentation. Clinical evaluations are performed using to the following scale:

None (1): No evidence of irregular pigmentation changes.
Mild (2): Minimal evidence—in both extent and noticeability in contrast with surrounding normal skin—of diffuse reticulated, irregular pigmentation changes, solar lentigines, or discrete hypo/hyperpigmentated macules.
Moderate (3): Moderate evidence of one or more of the following findings: moderate diffuse reticulated, irregular pigmentation changes, solar lentigines, or discrete hypo/hyperpigmentated macules.
Severe (4): One or more of the following findings: Extensive reticulated background irregular pigmentation changes, large discrete hypo/hyperpigmentated macules, or solar lentigines.

Evaluation scores are analyzed to establish statistical significance of changes in evaluation scores (a) over the course of the study (baseline vs. end of study), and (b) with respect to placebo (ALDARA vs. placebo). At the end of 4 to 8 weeks, improvement of age spots is clinically discernible. After 4 to 6 months of topical treatment, substantial improvement of age spots is observed in the majority of subjects tested. Complete eradication of age spots is observed after 6 to 9 months of topical administration with the IRM compositions of the instant inventions.

The complete disclosures of the patents, patent documents and publications cited herein are incorporated by reference in their entirety as if each were individually incorporated. In case of conflict, the present specification, including definitions, shall control. Various modifications and alterations to this invention will become apparent to those skilled in the art without departing from the scope and spirit of this invention. Illustrative embodiments and examples are provided as examples only and are not intended to limit the scope of the present invention. The scope of the invention is limited only by the claims set forth as follows.

What is claimed is:

1. A method of visibly reducing a human skin wrinkle comprising: topically applying to the human skin wrinkle an imiquimod composition comprising 5% imiquimod by weight for a period of time sufficient to visibly reduce the wrinkle, wherein imiquimod is the sole active pharmaceutical ingredient applied to the human skin wrinkle in performance of the method.

2. The method of claim 1, wherein the imiquimod composition is applied daily.

3. The method of claim 1, wherein the imiquimod composition is applied once per day two to three times a week.

4. The method of claim 1, wherein the imiquimod composition is applied to the human skin wrinkle for about one month.

5. The method of claim 1, wherein the imiquimod composition is applied to the human skin wrinkle for about two months.

6. The method of claim 1, wherein the imiquimod composition is applied to the human skin wrinkle for about 4 to 12 months.

7. The method of claim 1, further comprising measuring the reduction in human skin wrinkles by visual or photographic examination of the skin.

8. The method of claim 1, wherein the imquimod composition is about 5% imiquimod by weight, and the imiquimod composition is applied to the human skin wrinkle two to three times a week.

* * * * *